United States Patent [19]

Hahn et al.

[11] Patent Number: 4,715,057
[45] Date of Patent: Dec. 22, 1987

[54] X-RAY APPARATUS WITH SPRING WEIGHT COMPENSATION

[75] Inventors: Alfred Hahn, Erlangen; Bodo Kamm, Moehrendorf; Karl Weiss, Buckenhof; Johannes Dummert, Erlangen, all of Fed. Rep. of Germany

[73] Assignee: Siemens Aktiengesellschaft, Berlin and Munich, Fed. Rep. of Germany

[21] Appl. No.: 857,967

[22] Filed: May 1, 1986

[30] Foreign Application Priority Data

May 6, 1985 [DE] Fed. Rep. of Germany ... 8513305[U]

[51] Int. Cl.⁴ .................. G01N 21/00; G01N 21/34; G01N 23/00
[52] U.S. Cl. .................. 378/197; 378/193; 378/195; 378/196
[58] Field of Search .......... 378/197, 198, 195, 196, 378/193; 250/368 SF, 368 SC; 248/364, 297.1, 280.1, 274, 330.1, 327

[56] References Cited

U.S. PATENT DOCUMENTS

| 2,901,202 | 8/1959 | Stava et al. | 378/197 |
| 4,166,602 | 9/1979 | Nilsen | 378/197 |
| 4,590,378 | 5/1986 | Platz | 378/198 |

FOREIGN PATENT DOCUMENTS

| 1728886 | 8/1956 | Fed. Rep. of Germany |
| 968324 | 2/1958 | Fed. Rep. of Germany |
| 1047988 | 12/1958 | Fed. Rep. of Germany |

Primary Examiner—Carolyn E. Fields
Assistant Examiner—Joseph A. Hynds
Attorney, Agent, or Firm—Hill, Van Santen, Steadman & Simpson

[57] ABSTRACT

The invention relates to an x-ray apparatus comprising an apparatus base, a tiltable part, a displaceable carriage for x-ray parts running on the tiltable part along guide rails and having a spring weight compensation device having compensating forces adjustable by motor drive depending on the apparatus position, whereby at least one slot-shaped opening is provided on the carriage, one end of a one-armed load lever hinged to the tiltable part being displaceable in the slot-shaped opening. Between its ends, the load lever is pivotably connected to a sleeve seated in gliding fashion on a rod, the sleeve being supported with a spring at the one end of the rod whose other end is hinged to a nut displaceable by means of a motor-actuatable spindle, whereby the threaded spindle is arranged essentially parallel to the guide rails.

9 Claims, 3 Drawing Figures

X-RAY APPARATUS WITH SPRING WEIGHT COMPENSATION

BACKGROUND OF THE INVENTION

1. Field of the Invention

The invention relates to an x-ray apparatus comprising an apparatus base, a tiltable part, a displaceable carriage for x-ray parts running on the tiltable part along guide rails and having a spring weight compensation or a spring counterbalance having compensation forces which are adjustably motor-driven depending on the apparatus position.

2. Description of the Prior Art

German Pat. No. 968 324 discloses an x-ray apparatus including a spring weight compensation apparatus wherein the weight acting at a load lever is compensated by the counter-force of a single spring attacking at the load lever. The point of attack of the spring is displaced via a crank mechanism for setting the different opposing force required dependent upon the oblique position of the apparatus. Since the range of adjustment of the crank is relatively small but the parts to be moved and their weights are rather great, the compensation cannot be accomplished with the required reliability. Further, a cam is required for achieving a roughly constant spring power given differing positioning of the weight-compensated carriage with a target means or a spotfilm device. A precisely constant spring power, however, is thereby not obtainable. Further, such cams are very difficult to manufacture.

German AS No. 1 047 988 has proposed the displacement of the attack point of the spring weight compensation by means of a spindle driven by a regulating motor, so that a compensation can ensue in accord with the oblique position of the apparatus. A matching of the opposing force to the weight to be compensated is likewise achieved here by cam elements for required longitudinal movements in the direction of the spring compensation.

SUMMARY OF THE INVENTION

The present invention is based on an object of creating an x-ray apparatus of the type described above which is distinguished by a small structural size given the greatest possible stroke or lift and wherein only one adjustment element for the spring weight compensation is provided for setting the spring weight compensation dependent on the stroke or lift, the oblique position and the weight to be compensated.

This object is achieved in accord with the invention in that at least one slot-shaped opening is formed in the carriage, the one end of a one-armed load lever hinged to the tiltable part being displaceable in the slot-shaped opening; in that, between its ends, the lever is pivotably connected to a sleeve seated in gliding fashion on a rod, this sleeve being supported with a spring at the one end of the rod whose other end is hinged to a nut adjustable by means of a motor-actuatable threaded spindle, whereby the threaded spindle is arranged essentially parallel to the guide rails. What can thereby be achieved is that, dependent on the oblique position, the point of attack of the motor-adjustable nut and, thus, the opposing force generated by the spring are adjustable, whereby, however, the torque at the load lever produced by the spring remains constant independent of the stroke or lift.

An advantageous structure derives when the spring weight compensation for a target or sighting device carriage is arranged in the inside of a guide tower. A compensation in longitudinal direction of a table with great stroke or lift can be achieved when the spring weight compensation is arranged in a motor-displaceable longitudinal carriage within a tilting table. A simple control is obtained when a motor is attached to the threaded spindle, this motor being connected to a control circuit, and when the apparatus base has an angle sensor allocated to it and the threaded spindle has a length sensor allocated to it which are connected to the control circuit, so that the force to be compensated which can be set by means of the motor-driven threaded spindle proceeds with a sinusoidal angle function. The stroke or lift of the spring weight compensation arranged on the longitudinal carriage can be increased when a further sensor is attached to the load lever, this further sensor supplying a signal corresponding to the deviations of the load lever from its middle position to a further control circuit which controls the motor for the longitudinal carriage such that the deviation is compensated.

BRIEF DESCRIPTION OF THE DRAWINGS

The invention is set forth in greater detail below with reference to an exemplary embodiment shown in the drawing. Shown therein are.

DESCRIPTION OF THE PREFERRED EMBODIMENTS

Figures 1, 3:
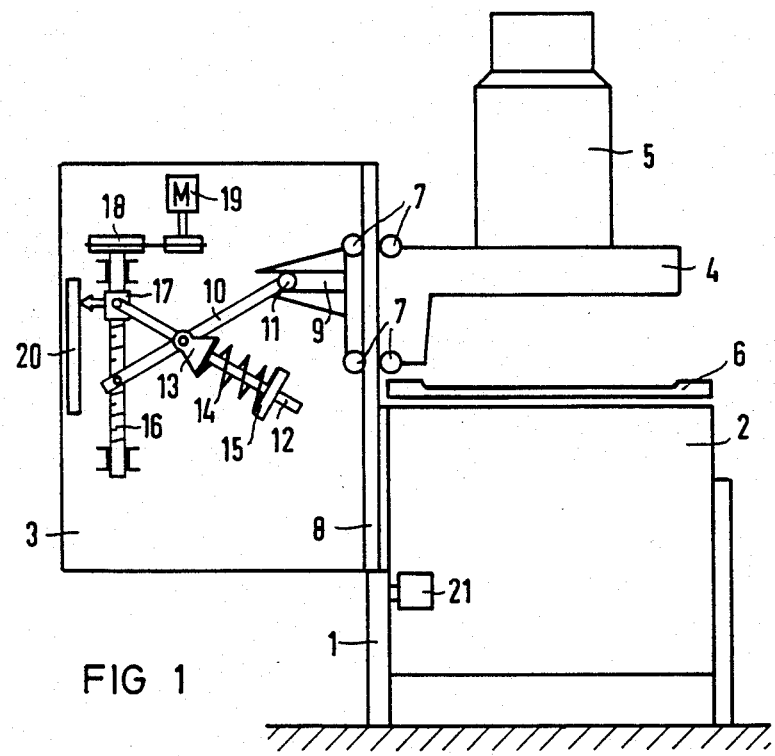
FIG. 1 is a schematic end elevational diagram of an x-ray apparatus of the invention.
FIG. 3 is a block circuit diagram of the control of the spring weight compensation of an x-ray apparatus of the invention.

FIG. 1 shows an x-ray apparatus comprising a tilting table 2 rotatably secured to an apparatus base 1, a guide tower 3 for a target or sighting device carriage 4 being attached to the tilting table 2, this carrying the target or sighting device 5 with the x-ray image intensifier video chain. A patient support plate 6 is movably attached to the tilting table 2. For greater clarity, the guide tower 3 is shown pivoted by 90°. The tilting table 2 and the guide tower 3 form a tiltable part.

The target or sighting device carriage 4, supported by rollers 7, runs along guide rails 8 in the guide tower 3. At its inside part, the target or sighting device carriage 4 includes a slot-shaped opening 9 in which a roller 11 attached to a one-armed load lever 10 glides. At its other end, the load lever 10 is rotatably connected to the guide tower 3. Between its two ends, the load lever 10 is pivotably connected to a sleeve 13 seated in sliding fashion on a rod 12, this sleeve 13 being supported via a spring 14 held by a fastening member 15 attached to the end of the rod 12. The other end of the rod 12 is connected in articulated fashion to a nut 17 which is movably adjustable by means of a threaded spindle 16. The threaded spindle 16 is driven by a motor 19 via a reducing gear 18. It proceeds parallel to the guide rails 8 and through the pivot point of the load lever 10. A length sensor 20 which is coupled to the nut 17 identifies the momentary position of the nut 17. An angle sensor 21 is attached to the tilting table 2, this angle sensor 21 being coupled to the device base 1 and determines the oblique position of the tilting table 2.

Figure 2:
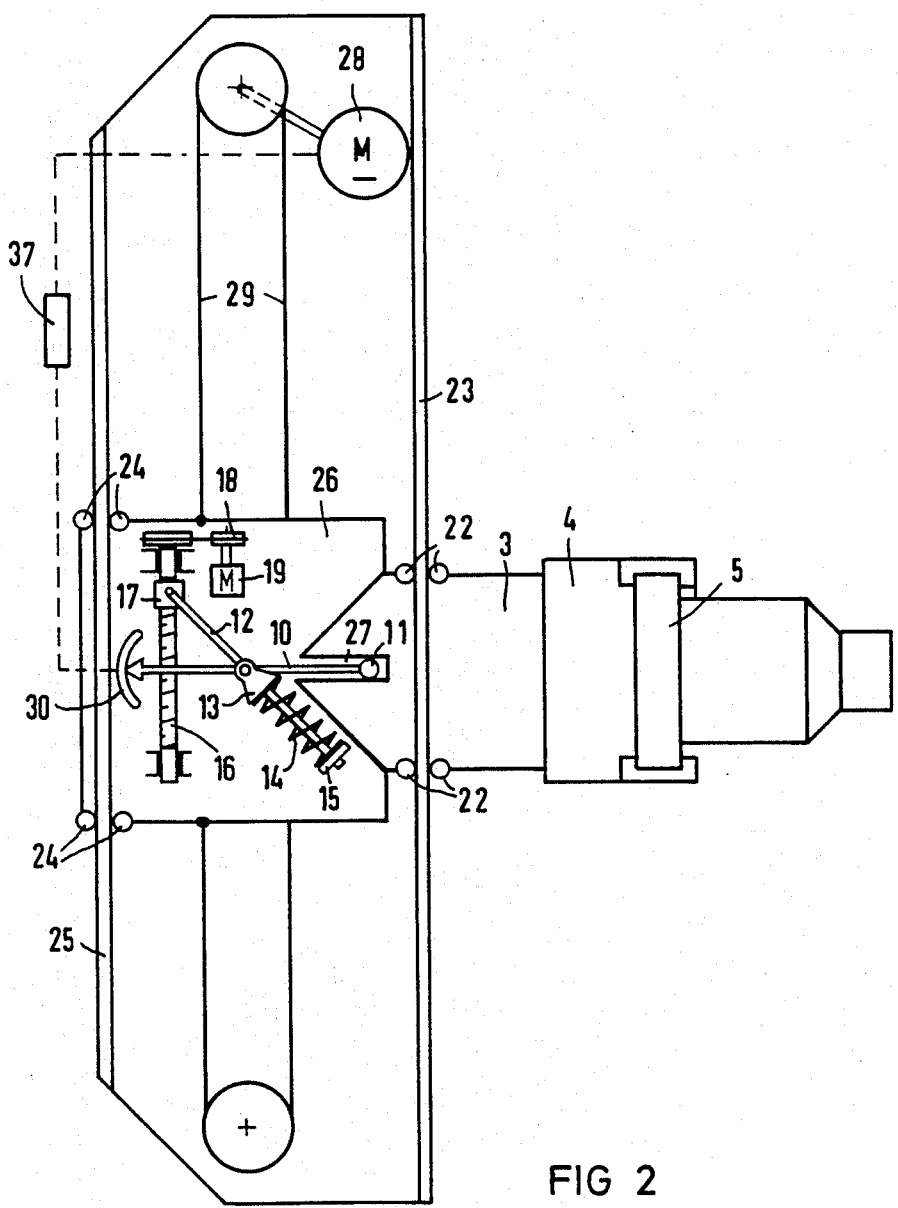
FIG. 2 is a section through the longitudinal table of the x-ray diagnostic installation of FIG. 1.

A further application of the spring weight compensation device of the invention is shown in FIG. 2, this compensating the guide tower 3 with target or sighting device 5 running on rollers 22 along guide rails 23. The spring weight compensation device is arranged on a longitudinal carriage 26 running on rollers 24 in guide rails 25. Its load lever 10 engages into a slot-shaped opening 27 provided in an inside part of the guide tower 3. This is displaced via a chain 29 driven by a motor 28, this chain 29 being connected to the longitudinal carriage 26, being displaced such that the load lever 10 is always aligned in its middle position, as shown, given the desired position of the guide tower 3. The position of the load lever 10 is identified by means of a sensor 30 coupled thereto.

The manner of functioning of the spring weight compensation shall be set forth in greater detail with reference to FIG. 3 which shows a block circuit diagram of the control of the spring weight compensation. The angle sensor 21 supplies a signal corresponding to the angle of the tilting table 2, supplying this signal via an analog-to-digital converter 31 to a function memory 32 in which the sine, or respectively, cosine function is contained. The cosine function is required for the spring weight compensation of FIG. 1 and the sine function is required for the spring weight compensation of FIG. 2, since, given a fold angle of ±90°, a compensation in a direction facing away from the tilting table 2 has to ensue only in case 1 and must ensue in both directions in case 2.

Via a digital-to-analog converter 33, the output signal of the function memory 32 is supplied to a first comparison stage 34 which is connected to an amplifier stage 35 for the motor 19. Via the reducing gear 18, the threaded spindle 16 and the nut 17, the motor 19 is mechanically connected to the length sensor 20 which supplies a signal proportional to the position of the nut 17 to a second comparison stage 36. The second input of the second comparison stage 36 is supplied with adjustable values A which correspond to the stages of enlargement and, thus, to the weight of the target or sighting device 5 and, thus, represent the rated value for the opposing force to be set. The second comparison stage 36 is connected to the second input of the first comparison stage 34 and supplies it with a controlled variable corresponding to the deviation of the force to be compensated from the rated value. This is compared to the angle function and the nut 17 is appropriately adjusted by the motor 19, so that the opposing force acting at the end of the load lever 10 completely compensates the weight of the carriage to be compensated.

Since, due to the compact structure, the stroke or lift of the spring weight compensation is limited, this is increased by the displaceable longitudinal carriage 26 in the exemplary embodiment of FIG. 2. When, for example, the person carrying out the examination displaces the guide tower at the control arm of the target or sighting device, then the load lever 10 is moved out of its middle position. This change in position is recognized by the sensor 30 which supplies a signal to a further control circuit 37 which engages the motor 28 in response thereto, so that the longitudinal carriage 26 is readjusted until the load lever 10 is again situated in its illustrated middle position. Adequate reserves in the readjustment are thus available, even if the person conducting the examination were to carry out a rapid movement. The setting of the spring weight compensation ensues in the same fashion as set forth with reference to FIG. 3.

What is achieved as a consequence of the geometrical arrangement of the load lever 10, of the rod 12 and of the threaded spindle 16 is that, after adjustment of the nut 17 by the threaded spindle 16 and the compensation of the weight of the carriage which has thereby ensued at the point of attack of the load, at the roller 11 of the load lever 10, the same moment occurs in every position of the load lever 10, so that the compensating force remains contant.

As is apparent from the foregoing specification, the invention is susceptible of being embodied with various alterations and modifications which may differ particularly from those that have been described in the preceding specification and description. It should be understood that we wish to embody within the scope of the patent warranted hereon all such modifications as reasonably and properly come within the scope of our contribution to the art.

We claim as our invention:

1. An x-ray apparatus comprising an x-ray source, an x-ray detector, an apparatus base, a tiltable part, a displaceable carriage for x-ray parts running on said tiltable part along guide rails and having a spring weight compensation device with compensating forces adjustably motordriven dependent on the apparatus position, comprising the improvement that said carriage has at least one slot shaped opening, one end of a one-armed load lever hinged to said tiltable part being displaceable in said slot-shaped opening; in that, between its ends, said load lever is pivotably connected to a sleeve seated in gliding fashion on a rod, said sleeve being supported with a spring at one end of said rod whose other end is hinged to a nut displaceable by means of a motor-actuatable threaded spindle, said threaded spindle being arranged essentially parallel to said guide rails.

2. An x-ray apparatus according to claim 1, including a target or sighting device carriage and a guide tower wherein said spring weight compensation device for said target or sighting device carriage is arranged in the inside of said guide tower.

3. An x-ray apparatus according to claim 1, including a tilting table wherein said spring weight compensation device is arranged in a motor-displaceable longitudinal carriage inside said tilting table.

4. An x-ray apparatus according to claim 1, wherein a motor is attached to said threaded spindle, said motor being connected to a control circuit and in that said apparatus base has an angle sensor and said threaded spindle has a length sensor allocated to it, these sensors being connected to said control circuit, so that the force to be compensated which can be set by said threaded spindle proceeds with a sine shaped angle function.

5. An x-ray apparatus according to claim 2, wherein a motor is attached to said threaded spindle, said motor being connected to a control circuit and in that said apparatus base has an angle sensor and said threaded spindle has a length sensor allocated to it, these sensors being connected to said control circuit, so that the force to be compensated which can be set by said threaded spindle proceeds with a sine shaped angle function.

6. An x-ray apparatus according to claim 3, wherein a motor is attached to said threaded spindle, said motor being connected to a control circuit and in that said apparatus base has an angle sensor and said threaded spindle has a length sensor allocated to it, these sensors being connected to said control circuit, so that the force to be compensated which can be set by said threaded spindle proceeds with a sine shaped angle function.

7. An x-ray apparatus according to claim 3, wherein a sensor is attached to said load lever, said sensor supplying a signal corresponding to the deviations of said load lever from its middle position to a control circuit which controls the motors for said longitudinal carriage such that the deviation is compensated.

8. An x-ray apparatus according to claim 6, wherein a further sensor is attached to said load lever, said further sensor supplying a signal corresponding to the deviations of said load lever from its middle position to a further control circuit which controls the motors for said longitudinal carriage such that the deviation is compensated.

9. An x-ray apparatus comprising:
   an x-ray source and an x-ray detector;
   an apparatus base;
   a tiltable part attached to said base;
   guide rails mounted on said tiltable part;
   a displaceable carriage supporting x-ray parts for moving along said guide rails on said tiltable part; said carriage having a slot-shaped opening therein;
   a spring weight compensation device for said carriage for providing compensating forces adjustably dependent on the position of the tiltable part;
   a load lever hinged to said tiltable part at one end and being displaceable in said slot-shaped opening at an opposite end;
   a threaded spindle journaled for rotation about its longitudinal axis which is positioned generally parallel to the longitudinal axis of said guide rails;
   a motor having a driving engagement with said spindle to cause said spindle to rotate about its longitudinal axis;
   a nut captured on said spindle;
   a rod pivotally attached at one end to said nut;
   a sleeve slidingly carried on said rod intermediate the ends of said rods;
   a spring carried on said rod engageable at one end with said sleeve and at an opposite end held fixed relative to said rod to urge said sleeve toward said nut;
   said load lever being pivotally attached intermediate its ends to said sleeve such that said spring will provide a biasing force intermediate the ends of said load lever;
   said nut being held against rotation so as to generate a reciprocating movement of said nut on said spindle upon operation of said motor;
   an angle sensor operable to detect the angle of said tiltable part;
   a length sensor operable to detect the position of said nut on said spindle;
   a control circuit for controlling said motor; the output of said sensors being connected to said control circuit;
   said motor, said spindle and said nut forming an arrangement for adjusting the biasing force of said spring by movement of said nut so as to generate the desired weight compensation for said carriage.

* * * * *